(12) United States Patent
Preininger

(10) Patent No.: US 7,790,472 B2
(45) Date of Patent: Sep. 7, 2010

(54) FIXED SUPPORT FOR IMMOBILIZING BIOMOLECULES

(75) Inventor: Claudia Preininger, Graz (AT)

(73) Assignees: Austrian Research Centers GmbH, Vienna (AT); Tecnet Capital Technologiemanagement GmbH, St. Polten (AT)

( * ) Notice: Subject to any disclaimer, the term of this patent is extended or adjusted under 35 U.S.C. 154(b) by 0 days.

(21) Appl. No.: 10/490,543

(22) PCT Filed: Sep. 24, 2002

(86) PCT No.: PCT/AT02/00277

§ 371 (c)(1), (2), (4) Date: Mar. 24, 2004

(87) PCT Pub. No.: WO03/027675

PCT Pub. Date: Apr. 3, 2003

(65) Prior Publication Data

US 2004/0259272 A1 Dec. 23, 2004

(30) Foreign Application Priority Data

Sep. 24, 2001 (AT) .............................. A 1508/2001

(51) Int. Cl.
*G01N 33/547* (2006.01)
*G01N 33/545* (2006.01)
*G01N 33/544* (2006.01)
*G01N 33/53* (2006.01)
*C12M 1/34* (2006.01)

(52) U.S. Cl. ................. 436/532; 436/531; 436/528; 435/7.92; 435/287.2

(58) Field of Classification Search .................. 435/6, 435/7.1, 7.9, 7.92, 180–181, 287.1, 287.2, 435/287.9, 288.3, 973; 422/57–58, 61, 68.1; 436/524, 528, 531–532

See application file for complete search history.

(56) References Cited

U.S. PATENT DOCUMENTS

| 4,225,410 A | * | 9/1980 | Pace | 204/412 |
| 4,245,064 A | | 1/1981 | Drobnik et al. | 525/329 |
| 4,881,109 A | * | 11/1989 | Ogawa | 257/253 |

(Continued)

FOREIGN PATENT DOCUMENTS

DE 24 38 436 2/1976

(Continued)

OTHER PUBLICATIONS

US Department of Energy Office of Science, Office of Biological and Environmental Research, Human Genome Program. [website] http://www.ornl.gov/sci/techresources/Human_Genome/glossary/glossary.shtml, accessed Mar. 22, 2005.*

(Continued)

*Primary Examiner* — Shafiqul Haq
(74) *Attorney, Agent, or Firm* — Fulbright & Jaworski LLP

(57) ABSTRACT

The invention concerns a fixed support for immobilizing biomolecules, said support being covered, at least in some parts, with a polymer. The invention is characterized in that the polymer is an epoxy resin with functionality ranging between 4 and 15. The invention also concerns a method for making such a support.

18 Claims, 4 Drawing Sheets

U.S. PATENT DOCUMENTS

| | | | | |
|---|---|---|---|---|
| 4,994,373 | A | * | 2/1991 | Stavrianopoulos et al. ...... 435/6 |
| 5,054,872 | A | * | 10/1991 | Fan et al. .................... 385/130 |
| 5,198,493 | A | | 3/1993 | Holmberg .................. 525/54.1 |
| 5,238,810 | A | | 8/1993 | Fujiwara et al. ................ 435/5 |
| 5,741,644 | A | * | 4/1998 | Kambara et al. ............... 435/6 |
| 5,962,136 | A | | 10/1999 | Dewez et al. ............... 428/410 |
| 6,150,103 | A | | 11/2000 | Ness et al. ..................... 435/6 |
| 6,228,326 | B1 | * | 5/2001 | Boxer et al. ............. 422/82.02 |
| 6,576,478 | B1 | * | 6/2003 | Wagner et al. ............. 436/518 |
| 6,582,662 | B1 | * | 6/2003 | Kellogg et al. ................ 422/72 |
| 2001/0024788 | A1 | * | 9/2001 | Hashimoto .................... 435/6 |
| 2002/0115224 | A1 | * | 8/2002 | Rudel et al. ................. 436/164 |

FOREIGN PATENT DOCUMENTS

| | | |
|---|---|---|
| GB | 2 125 963 | 3/1984 |
| WO | WO 94/00600 | 1/1994 |
| WO | WO 01/67129 | 9/2001 |

OTHER PUBLICATIONS

Adessi et al., "Solid phase DNA amplification: characterisation of primer attachment and amplification mechanisms," *Nucleic Acids Research*, 28(20):e87, 1-8,, 2000.

Canadian Office Action, issued in Canadian Application No. 2,460,981, mail date Nov. 12, 2009.

* cited by examiner

FIXED SUPPORT FOR IMMOBILIZING BIOMOLECULES

This application is a national phase application under 35 U.S.C. §371 of International Application No. PCT/AT02/00277 filed 24 Sep. 2002, which claims priority to Austrian Application No. A 1508/2001 filed 24 Sep. 2001, the contents of which are incorporated herein by reference in their entirety.

The present application relates to a solid support for immobilizing biomolecules which is at least partially coated with a polymer, as well as to a process for producing such carrier and to the use of an epoxy resin.

A variety of different solid supports for immobilizing bio-molecules is already known, wherein the prior art describes a variety of different forms and compositions. In order to be suitable for immobilizing bio-molecules, a carrier either has to be made of a suitable material or—as it is the case more and more often—the solid support is made of any material and the surface of it is coated with a specifically selected suitable material. The prior art describes a variety of materials for coating solid supports:

For example, U.S. Pat. No. 6,150,103 discloses an array for bio-molecules, wherein a layer of polyethylenimine (PEI) is applied on the surface of the array on a glass slide via a coupling agent such as Tri(O—$C_1$-$C_5$-alkyl) silane.

WO 94/00600 describes solid supports for nucleic acid hybridization assays wherein the solid carrier is coated with a polymer such as PEI.

According to the publication of Adessi et al. (Nucleic Acid Research, 2000, vol. 28, no. 20, e87) primers for conducting a solid phase PCR are bound to aminoderivated glass slides. Binding is carried out e.g. via S-MBS (m-maleic imidobenzoyl-n-hydroxysulfon-subtinimide ester).

In U.S. Pat. No. 5,962,136 a solid carrier is described on which a polymer is applied, wherein this polymer consists among other things of polyacryl, polyester, polyurethane, polysilicone, cellulose, epoxy, olefin, fluorine etc. On this polymeric layer, proteins or fragments thereof are immobilized.

According to WO 01/67129 A2 epoxy polymers are applied onto a carrier, which have been made e.g. of the following monomers: acryles, acrylamide derivatives, vinyles, nylon, polyurethanes and polyethers as well as copolymers thereof. These copolymers are preferably hydrophilic. The functionality is at least 1.

The object of the present invention is to provide a coating for a solid carrier for immobilizing biomolecules which has a low or negligibly low inherent fluorescence, a high immobilization capacity and a high signal-to-noise ratio after hydridization. Furthermore, the material for coating should be easy to produce and inexpensive, easy to apply on the solid carrier and suitable for a variety of different biomolecules, on DNA as well as protein level.

The object of the present invention is achieved by the initially described solid carrier characterized in that the polymer is a phenolic resin with a functionality of from 6 to 15, preferably from 7 to 10, particularly preferred 8. Surprisingly it has been found out that such an phenolic resin is perfectly suited as coating for a solid carrier for immobilizing biomolecules, has a low autofluorescence, a high immobilizing capacity as well as a very high signal-to-noise ratio. Phenolic resins with such a functionality are already known, however, so far they have been used in the field of semiconductors as well as an additive for solids, plastics, adhesives and other materials which have to withstand high temperatures.

Surprisingly, it has been found out that a phenolic resin with this kind of functionality is perfectly suited for immobilizing biomolecules, on DNA as well as protein level. Experts use the term "functionality" for describing the reactivity of the molecules building up the polymer. In the present case the functionality concerns e.g. the number of epoxy groups per molecule. On the one hand, the high functionality of the polymer is especially suitable as thereby the binding capacity of the polymer is increased. On the other hand, the functionality of the polymer of the present invention is not too high to act disturbing. If the functionality is too high, there is, e.g., the risk that the reactive groups interact with each other and thus the structure of the polymer is adversely affected. Thus, if the functionality of the polymer is too high the consistence of the polymer would be adversely changed. Therefore, the above mentioned functionalities are optimal for the coating of a solid carrier for immobilizing biomolecules, especially for subsequent analytical methods with high temperatures for which such phenolic resins are most suitable, especially as there are no additional thermochemical or photoreactive groups necessary to bind the polymer on the surface of the carrier. Furthermore, the phenolic resin has a high storage stability, improved tearing properties as well as an especially high temperature and dimensional stability. The phenolic resin can also be provided with additives in order to improve or change certain properties.

The term "solid carrier" within the scope of the present invention means any solid carrier of any shape, size and of suitable material which is known to the person skilled in the art. This can be e.g. microwell plates, microarrays, filters, columns, membranes etc. Here it is possible to structurize the phenolic resin via radiation such as UV radiation so as to produce so called patterned surfaces.

Due to the high stability, rigidity, viscosity, heat resistance and hardness, phenolic resins are especially suitable as polymer for coating solid carriers for immobilizing biomolecules. Furthermore, phenolic resins have a low tendency to creep and a low thermal expansion coefficient. Solid carriers with epoxy phenolic resins with an above defined functionality have surprisingly been found out to be optimal in view of the inherent fluorescence and the signal-to-noise ratio after hybridization.

Another suitable solid carrier is characterized in that the polymer is a novolak. Novolaks are phenolic resins whose aromatic rings are linked via methylene bridges. They can be cured at elevated temperatures under cross-linkage after addition of curing agents such as formaldehyde. Novolaks are acid-catalytically produced polycondensation products of formaldehydes and phenoles and have no methylol groups. Novolak-coatings with above defined functionality have been surprisingly found out to be very suitable regarding the immobilizing capacity.

Preferably the polymer is made up of bisphenol A groups. Bisphenol A is a 2,2-bis(4-hydroxyphenyl)propane ($C_{15}H_{16}O_2$) with a melting temperature of 155-156° C. These polymers have a high temperature and dimensional stability which is suitable for the use in On-chip-PCR's as there is a repeated heating up and cooling down involved. Furthermore, these polymers have a high chemical resistance, flow stability and short press cycles. A polymer made up of bisphenol A groups with an epoxy functionality of from 6 to 15 has all the necessary properties of a coating for solid carriers for immobilising biomolecules:

low or negligibly low inherent fluorescence, whereby the inherent fluorescence is that of the empty carrier, whereby the choice of the quality of the solid carrier determines the autofluorescence of the carrier.

Furthermore, the immobilising capacity after blockage of the reactive groups is markedly high, for example at least 60%.

Furthermore, the signal-to-noise ratio after hybridization is very high.

One example for such a polymer is Epon Resin SU-8 of Shell (equivalent to Epikote 157 of Resolution). Epikote 157 is a polymeric solid phenolic resin with an average epoxide group functionality mean value of 8 and is bisphenol A-based. The viscosity is 1 to 6 Pa·s at 130° C. The molar weight of epoxy is from 195 to 230 g/eq and the epoxy group content is from 4348 to 5128 mmol/kg. The melting temperature is approximately 82° C., density 1.2 kg/l. This material has been found out to be optimal as coating for a solid carrier for immobilizing biomolecules. For instance, SU-8 has a degradation temperature of about 380° C. At the same time, SU-8 is particularly biocompatible and in the case where it is cross-linked, it is very difficult to fluidise and it is insoluble in most chemicals. It has been found out that SU-8 has a very good temperature and dimensional stability and is therefore perfectly suited as coating material.

Preferably, the carrier is a microwell plate. In this case, the coating is provided in each well such that certain biomolecules can be immobilised per well.

It is furthermore advantageous if the carrier is a microarray. This microarray can be of any shape or size, it may e.g. be provided in the form of a glass slide or a well. Here the biomolecules are immobilised in a high density so that such microarrays are to a high extend suitable for detection and analysis methods. Such microarrays are known in the art and an expert can select the respective optimal microarray depending on the biomolecule and amount of samples to be detected.

Preferably, the polymer is coated in spots on the carrier. These spots are localised areas with given diameter. Thus, a solid carrier is provided which can only immobilize biomolecules in the spots, so that an accurate and reproducible result is obtained with analytical methods with several samples. Furthermore, the necessary amounts of samples are limited.

An advantageous carrier is furthermore characterised in that the biomolecules are immobilised on the polymer. Thus a carrier with immobilised biomolecules is already provided, making additional preparation steps for preparation of the carrier superfluous and thus simplify analytical methods to be undertaken. Thereby biomolecules can be immobilised directly on the polymer surfaces or also via known cross-linkers. Furthermore, biomolecules can be immobilised on the polymeric surface via an additional derivatisation.

The biomolecules are preferably immobilised in spots on the polymer. Here the term "spots" means in term localised areas of a certain diameter, whereby advantageously per spot similar and/or identical biomolecules are immobilized. Thus, a variety of different biomolecules can be analyzed or detected simultaneously on a solid carrier, which can also be coated with polymer on its entire surface.

Especially preferred are biomolecules selected from the group consisting of oligonucleotides, proteins, peptides, antigens and antibodies. The term "oligonucleotides" means DNA as well as RNA molecules of any size, in particular of a size of between 5 and 70 nucleotides, with or without artificial modifications. The biomolecules react with the epoxy groups, whereby they are immobilised on the polymer. Thus, such solid carriers can be used e.g. for solid phase PCR's, hybridisation reactions, the detection of antigens and/or antibodies, enzymatical reactions etc.

A further aspect of the present invention relates to the use of an phenolic resin with a functionality of from 6 to 15, preferably from 7 to 10, most preferably 8, as coating on a solid carrier for immobilising biomolecules. Here the above mentioned definitions and preferred embodiments also apply. A phenolic resin with such a functionality has so far not been used as coating means for a solid carrier for immobilizing biomolecules. It has now been found out that a phenolic resin with a functionality of from 6 to 15 is especially suitable therefor and provides optimal results especially in view of the binding capacity, the signal-to-noise ratio and the autofluorescence. The phenolic resin can be provided in solid form which is e.g. dissolved in methyl ethyl ketone, or already as finished solution e.g. in γ-butyrolactone.

It is especially preferred if the polymer is a novolak and especially preferred if the polymer is based on bisphenol A groups.

A further aspect of the present invention relates to a method for producing an inventive carrier as described above, wherein a layer of phenolic resin with a functionality of from 6 to 15, preferably from 7 to 10, most preferably 8, is applied onto a carrier. This can be done by any known method which is also known to a person skilled in the art in the field of biochemistry. Also different carriers can be used, e.g. chips, microwell plates, biosensors etc.

BRIEF DESCRIPTION OF THE DRAWINGS

The present invention is described according to the following examples and figures to which, however, it shall not be limited, wherein FIG. 1 the reaction mechanism of the inventive carrier is shown.

EXAMPLE 1

Production of Epoxy Resin Slides for Oligoarrays

The glass slides are coated by dipping into 2% epoxy resin (functionality 8) (Shell Chemicals)/toluene solution under $N_2$ or 2% epoxy resin/methyl ethyl ketone (subsequently named "SU-8 slides").

Figure 1:
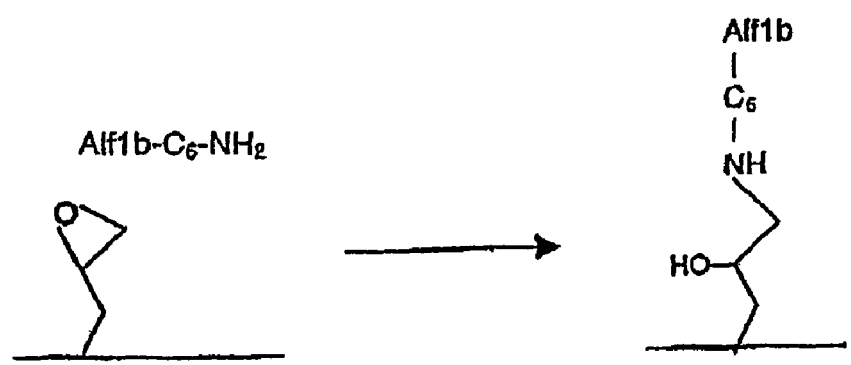

SU-8 slides contain epoxy functions which react with nucleophilic groups such as amino groups under ring openings to secondary amines. The reaction mechanism is shown in FIG. 1.

EXAMPLE 2

Hybridization Protocol

After spotting the amino-modified oligonucleotides, the SU-8 slides are applied on a damp paper tissue in a petri dish, sealed with Parafilm and left at 50° C. in a drying chamber over night. In this damp atmosphere the spots swell and can react with the reactive surface and can be bound covalently to the surface. After incubation in the drying chamber the slides can set-off for a few days before the blocking and hybridisation is started.

In order to block the reactive epoxy groups at the slide the slides are shaken with a solution of 50 mM ethanolamine, 0.1 M Tris, pH 9 and 0.1% SDS for 15 minutes at 50° C., washed again twice in $H_2O$ and subsequently blown dry with compressed air. It is suitable if at least 10 ml solution is used per slide and if the slides do not dry when changing the wash solution. For hybridising at the chip the sample labeled with Cy5 or Cy3 is taken up in 20 mM Tris, pH 7.4; 0.9 M NaCl, 0.01% SDS and formamide and denatured at 95° C. (5 min) and immediately put on ice. 20 µl are dropped onto the array at the slide, covered with a 1.5×1.5 cm covering plate and hybridised at 50° C.

Dependency of the Reactivity on the Polymer Concentration

Empty glass slides have been covered with 2%, 5% and 10% SU-8 solutions in toluene, spotted with 20 pM/µl Alf1b-$C_6$—$NH_2$ (5'CGTTCGYTCTGAGCCAG, 5' amino) and hybridised with 2 ng/µl Cy5-*rhizobium Fredii* after blockage of the reactive groups with ethanolamine. No differences in the hybridisation efficiency and in the signal-to-noise ratio were found.

Dependency of the Hybridisation Efficiency on the Hybridisation Time

Figure 2:
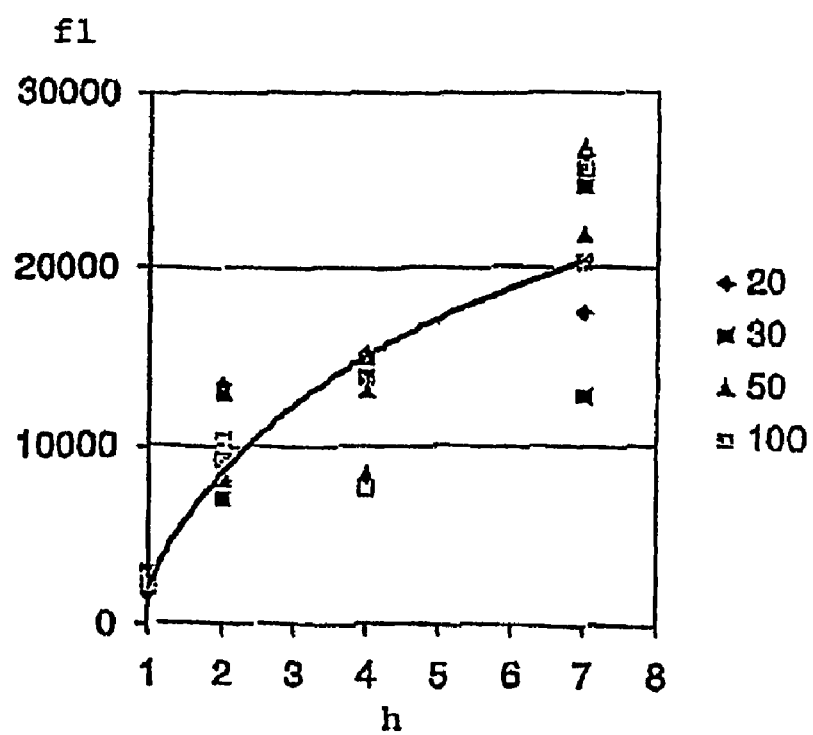
FIG. 2 the hybridisation genetics on the inventive carrier is shown.

The hybridisation times were varied from 1 to 7 h. FIG. 2 shows the fluorescence (fl) of the hybridisation signal as a function of time. A hybridisation time of 2 h is sufficient for an unambiguous hybridisation result. The intensities of fluorescence after 2 and 4 hour hybridisation are within the standard deviation.

Dependency of the Hybridisation Efficiency on Spot Volume

The hybridisation efficiency has been the same for 0.35 and 1 nl spots. The intensities of fluorescence did not change.

EXAMPLE 3

Immobilisation Capacity

In order to determine the immobilisation capacity K Cy5 labeled 17-mer oligonucleotides have been immobilised on SU-8 slides and the fluorescence intensity I has been measured after spotting, blocking and hybridisation. The immobilisation capacity is defined as $$K = 100 I_{after\ blockage\ and/or\ hybridisation} / I_{after\ spotting} \quad (1)$$

Figure 3:
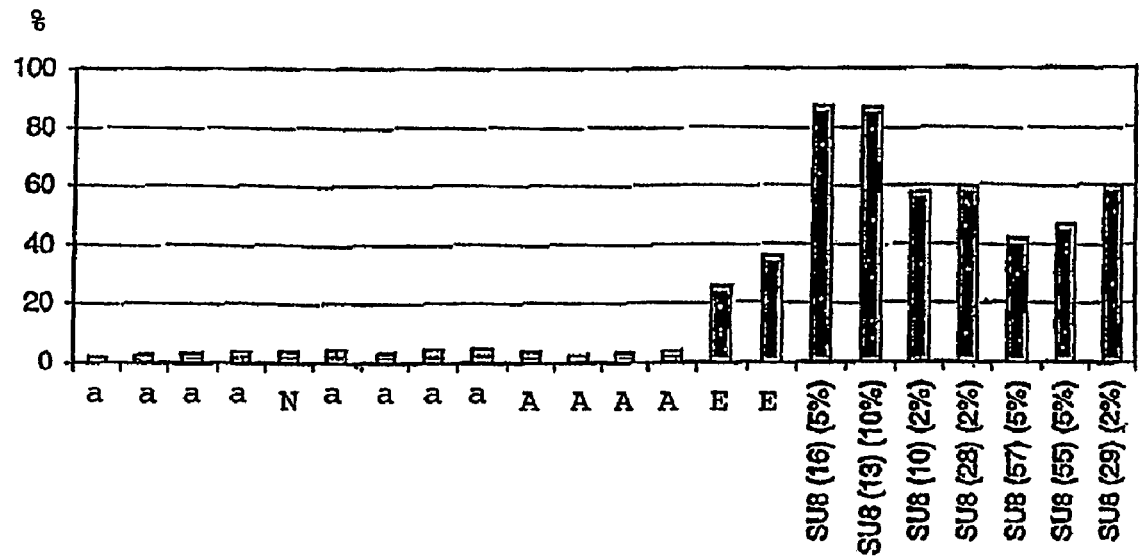
FIG. 3 the immobilisation capacity of biomolecules on commercial and on inventive carriers is shown.

In FIG. 3 the immobilising capacity on SU-8 slides is compared with aminosilanized (a), nitrocellulose (N), aldehyde (A), known epoxy slides (E) and SU-8 slides (SU). The SU-8 slides have shown the highest immobilising capacities, whereas it has to be considered that the same blockage reagent has only been used with known epoxy slides and SU-8 slides.

EXAMPLE 4

Dependency of the Immobilizing Capacity and the Hybridising Efficiency on the Spot Volume 0.35; 1 and 2 nl Cy5-labeled oligonucleotides have been spotted on SU-8 slides. The average spot diameter of an 350 pl spot is 100 µm. The spot diameter increases with the spot volume. The larger the spot, the more oligonucleotide can be immobilized. The fluorescence intensity does not change with the spot size. It is assumed that the spot is getting larger—only a little bit as the SU-8 surface is hydrophobic—when three drops are spotted on top of each other for 1 nl spot, but only a fractional amount of the applied amount reaches the SU-8 surface and can be immobilised. This assumption is confirmed by hybridisations of 0.35 nl and 1 nl Alf1b spots: In both cases the hybridisation efficiency is the same. Apart from that, the fluorescence intensity is according to the Lambert-Beer-Law dependent on the concentration but not on the amount.

EXAMPLE 5

Signal-to-Noise Ratio

Figure 4:
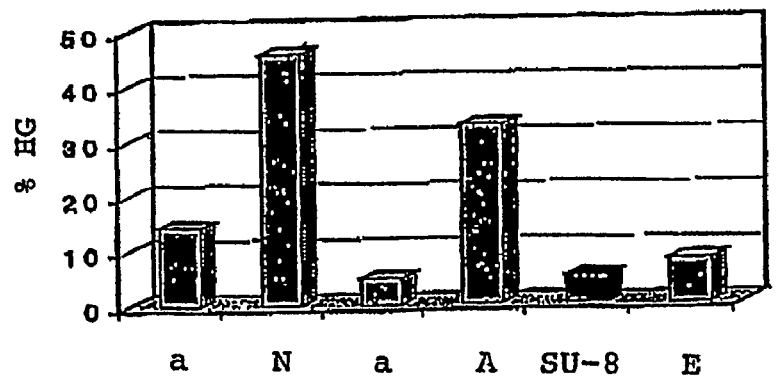
FIG. 4 the signal-to-noise ratio of different carriers is shown.

The fluorescence background on SU-8 slides is on average 5-10%. FIG. 4 is a comparison of the signal-to-noise ratio (HG, background) in %, wherein amino-silanized (a), nitrocellulose-(N), aldehyde (A), known epoxy slides (E) and SU-8 slides have been compared to each other. The SU-8 slides have a very good signal-to-noise ratio compared to the known slides.

These examples show that the inventive carriers for immobilising biomolecules are particularly efficient compared to known carriers and yield particularly results as regards the binding capacity, inherent fluorescence and background noise.

EXAMPLE 6

Fluorescence Background after Hybridisation

The fluorescence background has been calculated as percentage of the hybridisation signal, wherein the mean fluorescence background as measured by 15 hybridised samples on SU-8 has been 9.3%, on 3D-Link™ 29.9% and on EasySpot (hydrophilic epoxy polymer) 30.1%.

Figure 5:
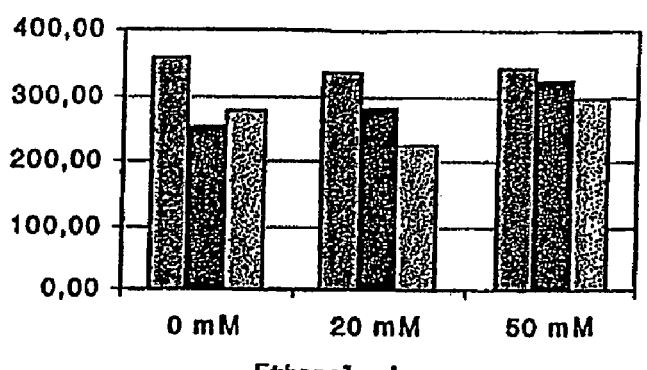
FIG. 5 a comparison of a hybridisation with and without ethanolamine blockage is shown.

Hybridization has been measured after blockage of the carrier with 0, 20 and 50 mM ethanolamine, wherein FIG. 5 shows that a hybridisation without ethanolamine blockage resulted in a similar fluorescence background, as compared to hybridisation with ethanolamine blockage. Due to that the method with SU-8 can also be carried out without the blockage step considerably facilitating and shortening the method, as compared to common carriers in which the blockage step is essential.

EXAMPLE 7

Spotter Compatibility

Figure 6:
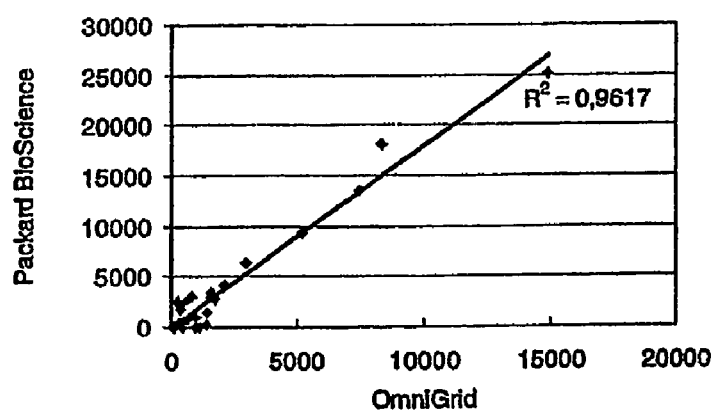
FIG. 6 the compatibility with two different spotters is shown.

SU-8 has been tested in an diagnostic assay in terms of spotter compatibility. 0.35 nl samples were spotted onto a carrier, whereby the piezoelectrical BioChip-Arrayer from Packard BioScience was used and 0.6 nl samples were spotted onto a carrier with the help of the OmniGrid from GeneMachines. FIG. 6 shows the hybridisation signals of the spotted samples, resulting in a distinguished correlation.

EXAMPLE 8

Spot Density

Figure 7:
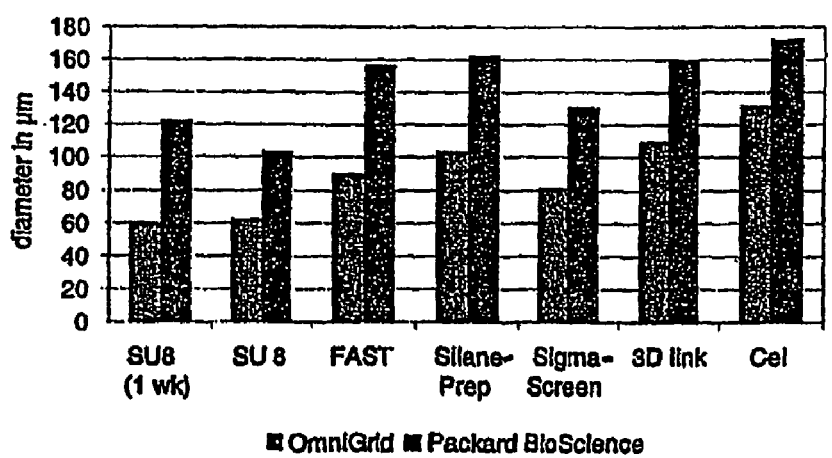
FIG. 7 a comparison of the spot diameters of different polymers is shown.

The mean spot diameter of biomolecular samples on different reactive chip surfaces was measured. The spots were applied, on the one hand, with OmniGrid and, on the other hand, with Packard BioScience, whereby FIG. 7 shows that the spots on SU-8 have a smaller diameter than the spots on conventional chip surfaces (whereas FAST=nitrocellulose, Silane-Prep and Sigma-Screen=amino-silanized, 3D-Link=known epoxy polymer and Cel=aldehyde). Due to the comparatively small spot diameter on SU-8, this polymer is especially suitable for high throughput applications as more spots per unit of area can be applied at shorter intervals on the surface.

EXAMPLE 9

Optimum Sample Concentration

Figure 8A:
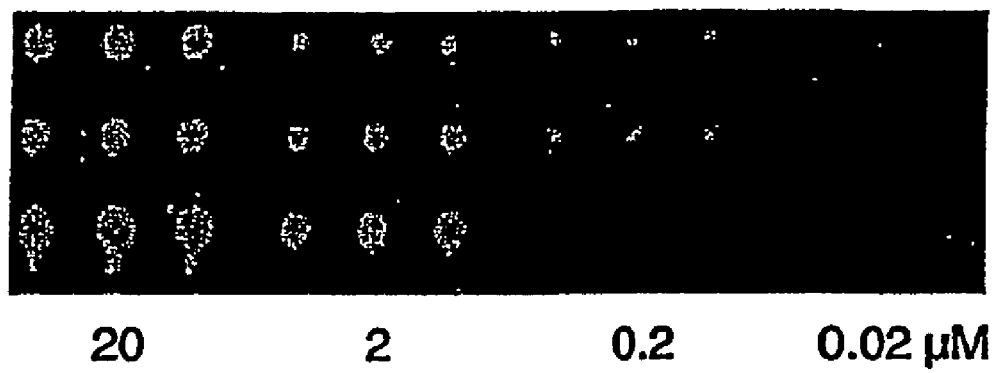
FIG. 8 the optimal sample concentration is shown.

The concentration of an amino-modified oligonucleotide (18 to 50 mer) spotted onto a SU-8 carrier was varied between 0.02 μM and 100 μM and the hybridisation signals were measured. No difference in the hybridisation fluorescence at higher concentrations (above 20 μM) could be detected. The lowest concentration of the sample which leads to a significant hybridisation signal was 2 μM. FIG. 8a shows the hybridisation fluorescence of 20, 2, 0.2 and 0.02 μM spotted oligonucleotides.

Figure 8B:
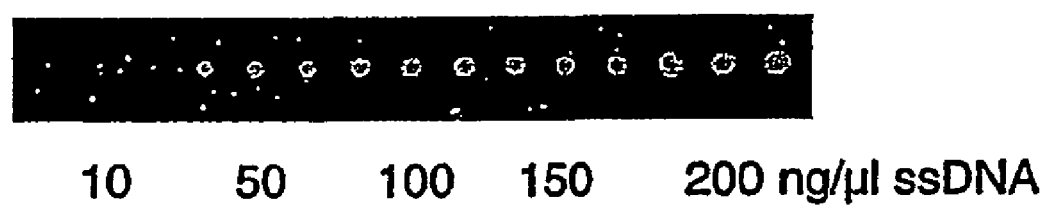

Furthermore, single strand DNA (1500 base pairs) were spotted onto a SU-8 carrier, wherein already at 50 ng/μl single strand DNA a detectable signal is visible. In FIG. 8b the result of the fluorescence scan can be seen, whereby 10, 50, 100, 150 and 200 ng/μl single strand DNA with 2 ng/μl fluorescence labelling has been spotted onto the carrier.

The invention claimed is:

1. A solid carrier comprising at least a partial polymer coat, comprising at least one biomolecule immobilized by the polymer, wherein the polymer is further defined as a phenolic resin having a functionality of from 6 to 15, wherein the biomolecules are immobilized by the functionality, and wherein the functionality concerns the number of epoxy groups per molecule.

2. The solid carrier of claim 1, wherein the polymer is a phenolic resin with a functionality of from 7 to 10.

3. The solid carrier of claim 2, wherein the polymer is a phenolic resin with a functionality of 8.

4. The solid carrier of claim 1, wherein the polymer is a epoxylated novolak.

5. The solid carrier of claim 1, wherein the polymer comprises bisphenol A groups.

6. The solid carrier of claim 1, wherein the carrier is a microwell plate.

7. The solid carrier of claim 1, wherein the carrier is a microarray.

8. The solid carrier of claim 1, wherein the polymer is coated in spots onto the carrier.

9. The solid carrier of claim 1, wherein the at least one biomolecule is immobilized in spots on the polymer.

10. The solid carrier of claim 1, wherein the at least one biomolecule is an oligonucleotide, a protein, a peptide, an antigen, or an antibody.

11. A method of immobilizing at least one biomolecule comprising obtaining a solid carrier comprising at least a partial polymer coat, and immobilizing the biomolecule with the polymer on the carrier, wherein the polymer is further defined as a phenolic resin having a functionality of from 6 to 15, wherein the biomolecule is immobilized by the functionality, and wherein the functionality concerns the number of epoxy groups per molecule.

12. The method of claim 11, wherein the polymer is a phenolic resin with a functionality of from 7 to 10.

13. The method of claim 12, wherein the polymer is a phenolic resin with a functionality of 8.

14. The method of claim 11, wherein the polymer is a epoxylated novolak.

15. The method of claim 11, wherein the polymer comprises bisphenol A groups.

16. A method of producing a solid carrier comprising at least a partial polymer coat according to claim 1, comprising applying a layer of phenolic resin having a functionality of from 6 to 15 onto a carrier, and further comprising binding at least one biomolecule with the polymer on the solid carrier, wherein the biomolecule is immobilized by the functionality, and wherein the functionality concerns the number of epoxy groups per molecule.

17. The method of claim 16, wherein the polymer is a phenolic resin with a functionality of from 7 to 10.

18. The method of claim 17, wherein the polymer is a phenolic resin with a functionality of 8.

* * * * *